(12) United States Patent
Cheng et al.

(10) Patent No.: US 11,880,972 B2
(45) Date of Patent: Jan. 23, 2024

(54) TISSUE NODULE DETECTION AND TISSUE NODULE DETECTION MODEL TRAINING METHOD, APPARATUS, DEVICE, AND SYSTEM

(71) Applicant: Tencent Technology (Shenzhen) Company Limited, Shenzhen (CN)

(72) Inventors: Chen Cheng, Shenzhen (CN); Zhongqian Sun, Shenzhen (CN); Zhao Chen, Shenzhen (CN); Wei Yang, Shenzhen (CN)

(73) Assignee: Tencent Technology (Shenzhen) Company Limited, Guangdong (CN)

( * ) Notice: Subject to any disclaimer, the term of this patent is extended or adjusted under 35 U.S.C. 154(b) by 517 days.

(21) Appl. No.: 17/093,022

(22) Filed: Nov. 9, 2020

(65) Prior Publication Data
US 2021/0056693 A1 Feb. 25, 2021

Related U.S. Application Data

(63) Continuation of application No. PCT/CN2019/115822, filed on Nov. 5, 2019.

(30) Foreign Application Priority Data

Nov. 8, 2018 (CN) .......................... 201811326267.4

(51) Int. Cl.
*G06F 18/22* (2023.01)
*G06V 10/764* (2022.01)
(Continued)

(52) U.S. Cl.
CPC .......... *G06T 7/0012* (2013.01); *G06F 18/213* (2023.01); *G06F 18/22* (2023.01);
(Continued)

(58) Field of Classification Search
CPC ....... G06F 18/213; G06F 18/22; G06N 20/10; G06N 3/045; G06N 3/08;
(Continued)

(56) References Cited

U.S. PATENT DOCUMENTS

| 2003/0210820 A1* | 11/2003 | Lachner | .................... G06T 7/74 382/209 |
| 2016/0078287 A1* | 3/2016 | Auge | ..................... G06V 20/49 382/103 |

(Continued)

FOREIGN PATENT DOCUMENTS

| CN | 107403201 A | 11/2017 |
| CN | 107871318 A | 4/2018 |

(Continued)

OTHER PUBLICATIONS

International Search Report and Written Opinion with English Translation for International Application No. PCT/CN2019/115822 dated Jan. 23, 2020; 13 pages.

(Continued)

*Primary Examiner* — Tsung Yin Tsai
(74) *Attorney, Agent, or Firm* — Crowell & Moring LLP

(57) ABSTRACT

This application relates to a tissue nodule detection and tissue nodule detection model training method, apparatus, device, storage medium and system. The method for training a tissue nodule detection model includes: obtaining source domain data and target domain data, the source domain data comprising a source domain image and an image annotation, the target domain data comprising a target image, and the image annotation being used for indicating location information of a tissue nodule in the source domain image; performing feature extraction on the source domain image using a neural network model to obtain a source domain sampling feature, performing feature extraction on the target image using the neural network model to obtain a target (Continued)

sampling feature, and determining a model result according to the source domain sampling feature using the neural network model; determining a distance parameter between the source domain data and the target domain data according to the source domain sampling feature and the target sampling feature, the distance parameter being a parameter describing a magnitude of a data difference between the source domain data and the target domain data; determining, according to the model result and the image annotation, a loss function value corresponding to the source domain image; and training the neural network model to obtain a tissue nodule detection model by iteratively reducing a combination of the loss function value and the distance parameter. In this way, the detection accuracy can be improved.

20 Claims, 5 Drawing Sheets

(51) Int. Cl.
*G06V 10/774* (2022.01)
*G06V 20/69* (2022.01)
*G06T 7/00* (2017.01)
*G06F 18/213* (2023.01)
*G06V 10/82* (2022.01)

(52) U.S. Cl.
CPC ........ *G06V 10/764* (2022.01); *G06V 10/7753* (2022.01); *G06V 10/82* (2022.01); *G06V 20/695* (2022.01); *G06V 20/698* (2022.01); *G06T 2207/20081* (2013.01); *G06T 2207/20084* (2013.01); *G06T 2207/30024* (2013.01)

(58) Field of Classification Search
CPC . G06T 2207/10081; G06T 2207/10088; G06T 2207/20081; G06T 2207/20084; G06T 2207/30024; G06T 2207/30064; G06T 7/0012; G06T 7/11; G06V 10/764; G06V 10/7753; G06V 10/82; G06V 20/695; G06V 20/698; G16H 30/40; G16H 50/20
See application file for complete search history.

(56) References Cited

U.S. PATENT DOCUMENTS

| | | | |
|---|---|---|---|
| 2018/0253627 A1* | 9/2018 | Baradel | G06F 18/24133 |
| 2019/0392547 A1* | 12/2019 | Katouzian | G06V 20/62 |
| 2020/0372635 A1* | 11/2020 | Veidman | G06T 7/194 |

FOREIGN PATENT DOCUMENTS

| | | |
|---|---|---|
| CN | 108460415 A | 8/2018 |
| CN | 109523526 A | 3/2019 |
| JP | 2018-117883 A | 8/2018 |
| JP | 2019-523504 A | 8/2019 |
| JP | 2020-071883 A | 5/2020 |
| WO | WO 2018/020277 A1 | 2/2018 |

OTHER PUBLICATIONS

Office Action for Chinese Patent Application No. 201811326267.4 dated Aug. 5, 2020; 11 pages.

Ghafoorain, Mohsen et al., "Transfer Learning for Domain Adaptation in MRI: Application in Brain Lesion Segmentation", arXiv:1702.07841v1 [cs.CV] Feb. 25, 2017; 8 pages.

Dou, Qi et al., "Unsupervised Cross-Modality Domain Adaptation of ConvNets for Biomedical Imagae Segmentation with Adersarial Loss", arXiv:1804.10916v2 [cs.CV] Jun. 19, 2018; 7 pages.

Wang, Mei et al., "Deep Visual Domain Adaptation: A Survey", arXiv:1802.03601v4 [cs.CV] May 25, 2018; 20 pages.

Ganin, Yaroslav et al., "Domain-Adversarial Training of Neural Networks", arXiv:1505.07818v4 [stat.ML] May 26, 2016, Journal of Machine Learning Research 17, Published Apr. 16, 2016; 35 pages.

Chu, Jinghui et al.: "Breast Cancer Diagnosis System based on Transfer Learning and Deep Convolutional Neural Networks", (*Laser & Optoelectronics Progress*), No. 8 , Aug. 31, 2018; ISSN: 1006-4125, English Abstract, 1 page.

Japanese Office Action with English Translation for Japanese Patent Application No. 2020-560811 dated Jan. 4, 2022, 5 pages.

Office Action with English Translation of Concise Explanation of Relevance for Chinese Patent Application No. 201811326267.4 dated May 18, 2021; 7 pages.

\* cited by examiner

TISSUE NODULE DETECTION AND TISSUE NODULE DETECTION MODEL TRAINING METHOD, APPARATUS, DEVICE, AND SYSTEM

RELATED APPLICATION

This application is a continuation application of the International PCT Application No. PCT/CN2019/115822, filed with the China National Intellectual Property Administration, PRC on Nov. 5, 2019 which claims priority to Chinese Patent Application No. 201811326267.4, entitled "TISSUE NODULE DETECTION METHOD AND APPARATUS, TISSUE NODULE DETECTION MODEL TRAINING METHOD AND APPARATUS, DEVICE, AND SYSTEM" and filed with the China National Intellectual Property Administration, PRC on Nov. 8, 2018, which are incorporated herein by reference in their entireties.

FIELD OF THE TECHNOLOGY

This application relates to the field of medical image processing technologies, and in particular, to a method, an apparatus, and a computer device for training a tissue nodule detection model, and a method, an apparatus, a computer device, and a system for tissue nodule detection.

BACKGROUND OF THE DISCLOSURE

Canceration of tissues is a leading cause of death, and therefore early detection and treatment are crucial. One strong indicator for determining a cancer is to determine whether a tissue has a nodule. Currently, whether there is a tissue nodule may be determined with the help of a medical image, such as a chest thin-section CT image, which causes a lot of workload on doctors. To reduce the burden on doctors, automatic recognition of a tissue nodule in a tissue image has become a very critical technology.

With the continuous development of artificial intelligence (AI), the tissue nodule in the tissue image may be recognized based on a convolutional neural network (CNN). However, medical imaging devices of hospitals are not uniform as they may be of different brands and models, and sampling distances, noise levels, and nodule diameter distributions of a captured tissue image dataset may be different, causing an image distribution in an actual detection effort to be different from an image dataset distribution in a training dataset.

Therefore, the conventional tissue nodule detection method has a problem of relatively poor accuracy.

SUMMARY

This application provides a method, an apparatus, and a computer device for training a tissue nodule detection model, and a method, an apparatus, a computer device, and a system for tissue nodule detection, which may improve the accuracy of tissue nodule detection.

A method for training a tissue nodule detection model is provided, including:

obtaining source domain data and target domain data, the source domain data including a source domain image and an image annotation, and the target domain data including a target image, the image annotation being used for indicating location information of a tissue nodule in the source domain image;

performing feature extraction on the source domain image through a neural network model to obtain a source domain sampling feature, performing feature extraction on the target image through the neural network model to obtain a target sampling feature, and determining a model result according to the source domain sampling feature;

determining a distance parameter between the source domain data and the target domain data according to the source domain sampling feature and the target sampling feature;

determining, according to the model result and the image annotation, a loss function value corresponding to the source domain image; and training the neural network model to obtain a tissue nodule detection model by iteratively reducing a combination of the loss function value and the distance parameter.

in this disclosure, when training the tissue nodule detection model, a model result may also be referred to as a training result.

An apparatus for training a tissue nodule detection model is provided, including:

a training data obtaining module, configured to obtain source domain data and target domain data, the source domain data including a source domain image and an image annotation, and the target domain data including a target image, the image annotation being used for indicating location information of a tissue nodule in the source domain image;

a feature extraction and training module, configured to perform feature extraction on the source domain image through a neural network model to obtain a source domain sampling feature, perform feature extraction on the target image through the neural network model to obtain a target sampling feature, and determine a training result according to the source domain sampling feature;

a distance parameter determining module, configured to determine a distance parameter between the source domain data and the target domain data according to the source domain sampling feature and the target sampling feature, the distance parameter being a parameter describing a magnitude of a data difference between the source domain data and the target domain data;

a source domain loss determining module, configured to determine, according to the training result and the image annotation, a loss function value corresponding to the source domain image; and a model determining module, configured to train the neural network model to obtain a tissue nodule detection model by iteratively reducing a combination of the loss function value and the distance parameter.

In an implementation, the distance parameter includes a discrepancy loss based on a maximum mean discrepancy (MMD); and the distance parameter determining module is configured to determine the MMD-based discrepancy loss between the source domain data and the target domain data according to the source domain sampling feature and the target sampling feature.

In an implementation, the distance parameter determining module is configured to determine, based on a Gaussian kernel function, the MMD-based discrepancy loss between the source domain data and the target domain data according to the source domain sampling feature and the target sampling feature.

In an implementation, the distance parameter determining module includes:

a first discrepancy loss unit, configured to determine a first MMD-based discrepancy loss between the source domain data and the target domain data according to the source domain sampling feature and the target sampling feature;

a candidate region determining unit, configured to perform target region extraction on the source domain sampling feature, to obtain a source domain candidate region, and perform target region extraction on the target sampling feature, to obtain a target candidate region;

a mapping result determining unit, configured to perform, after performing pooling processing on the source domain sampling feature and the source domain candidate region, mapping to obtain a source domain mapping result, and perform, after performing pooling processing on the target sampling feature and the target candidate region, mapping to obtain a target mapping result;

a second discrepancy loss unit, configured to determine a second MMD-based discrepancy loss and between the source domain data and the target domain data according to the source domain mapping result and the target mapping result; and a comprehensive discrepancy determining unit, configured to determine the MMD-based discrepancy loss and between the source domain data and the target domain data according to the first MMD-based discrepancy loss and the second MMD-based discrepancy loss.

In an implementation, the apparatus further includes: a total loss determining module, where the total loss determining module is configured to determine a total loss function value according to the loss function value and the distance parameter; and the model determining module is further configured to determine the tissue nodule detection model based on the total loss function value and the neural network model.

In an implementation, the distance parameter includes a square of the MMD; and the total loss determining module is configured to perform linear summation on the square of the MMD and the loss function value, to obtain the total loss function value.

In an implementation, the apparatus further includes: a tissue region segmentation module, where the tissue region segmentation module is configured to segment the source domain image, to obtain a source domain tissue region, and segment the target image, to obtain a target tissue region; and the feature extraction and training module is configured to perform feature extraction on the source domain tissue region through a neural network model, to obtain the source domain sampling feature, and perform feature extraction on the target tissue region through the neural network model, to obtain the target sampling feature.

In an implementation, the source domain image in the source domain data and the target image in the target domain data meet a quantity relationship.

In an implementation, the source domain image in the source domain data and the target image in the target domain data are equal in quantity.

In an implementation, the feature extraction and training module includes:

a feature extraction and training unit, configured to perform feature extraction on the source domain image through a first neural network model, to obtain the source domain sampling feature, and determine the training result according to the source domain sampling feature; and a feature extraction unit, configured to perform feature extraction on the target image through a second neural network model, to obtain the target sampling feature, a second neural network model and a first neural network model sharing a same weight.

A tissue nodule detection method is provided, including:
obtaining a to-be-detected image;
inputting the to-be-detected image into a tissue nodule detection model, to obtain nodule location information, the tissue nodule detection model being obtained according to a tissue nodule detection model training apparatus, and the to-be-detected image and the target image having the same data structure, the tissue nodule detection model training apparatus including: a training data obtaining module, configured to obtain source domain data and target domain data, the source domain data including a source domain image and an image annotation, and the target domain data including a target image, the image annotation being used for indicating location information of a tissue nodule in the source domain image; a feature extraction and training module, configured to perform feature extraction on the source domain image through a neural network model to obtain a source domain sampling feature, perform feature extraction on the target image through the neural network model to obtain a target sampling feature, and determine a training result according to the source domain sampling feature; a distance parameter determining module, configured to determine a distance parameter between the source domain data and the target domain data according to the source domain sampling feature and the target sampling feature, the distance parameter being a parameter describing a magnitude of a data difference between the source domain data and the target domain data; a source domain loss determining module, configured to determine, according to the training result and the image annotation, a loss function value corresponding to the source domain image; and a model determining module, configured to train the neural network model to obtain a tissue nodule detection model by iteratively reducing a combination of the loss function value and the distance parameter.

A tissue nodule detection apparatus is provided, including:

a to-be-detected image obtaining module, configured to obtain a to-be-detected image; and a detection model detection module, configured to input the to-be-detected image into a tissue nodule detection model, to obtain nodule location information, the tissue nodule detection model being obtained according to a tissue nodule detection model training apparatus, and the to-be-detected image and the target image having the same data structure, the tissue nodule detection model training apparatus including: a training data obtaining module, configured to obtain source domain data and target domain data, the source domain data including a source domain image and an image annotation, and the target domain data including a target image, the image annotation being used for indicating location information of a tissue nodule in the source domain image; a feature extraction and training module, configured to perform feature extraction on the source domain image through a neural network model to obtain a source domain sampling feature, perform feature extraction on the target image through the neural network model to obtain a target sampling feature, and determine a training result according to the source domain sampling feature; a distance parameter determining module, configured to determine a distance parameter between the source domain data and the target domain data according to the source domain sampling feature and the target sampling feature, the distance parameter being a parameter describing a magnitude of a data difference between the source domain data and the target domain data; a source domain loss determining module, configured to determine, according to the training result and the image annotation, a loss function value corresponding to the source domain image; and a model determining module, configured to train the neural network model to obtain a tissue nodule detection model by iteratively reducing a combination of the loss function value and the distance parameter.

A computer device is provided, including a memory and a processor, the memory storing a computer program, and the processor, when executing the computer program, implementing the following operations:

obtaining source domain data and target domain data, the source domain data including a source domain image and an image annotation, and the target domain data including a target image, the image annotation being used for indicating location information of a tissue nodule in the source domain image;

performing feature extraction on the source domain image through a neural network model to obtain a source domain sampling feature, performing feature extraction on the target image through the neural network model to obtain a target sampling feature, and determining a training result according to the source domain sampling feature;

determining a distance parameter between the source domain data and the target domain data according to the source domain sampling feature and the target sampling feature, the distance parameter being a parameter describing a magnitude of a data difference between the source domain data and the target domain data;

determining, according to the training result and the image annotation, a loss function value corresponding to the source domain image; and training the neural network model to obtain a tissue nodule detection model by iteratively reducing a combination of the loss function value and the distance parameter.

A computer device is provided, including a memory and a processor, the memory storing a computer program, and the processor, when executing the computer program, implementing the following operations:

obtaining a to-be-detected image;

inputting the to-be-detected image into a tissue nodule detection model, to obtain nodule location information, the tissue nodule detection model being obtained according to the tissue nodule detection model training method, and the to-be-detected image and the target image being taken under comparative conditions and having the same data structure.

A non-transitory computer-readable storage medium is provided, storing a computer program, the computer program, when executed by a processor, implementing the following operations:

obtaining source domain data and target domain data, the source domain data including a source domain image and an image annotation, and the target domain data including a target image, the image annotation being used for indicating location information of a tissue nodule in the source domain image;

performing feature extraction on the source domain image through a neural network model to obtain a source domain sampling feature, performing feature extraction on the target image through the neural network model to obtain a target sampling feature, and determining a training result according to the source domain sampling feature;

determining a distance parameter between the source domain data and the target domain data according to the source domain sampling feature and the target sampling feature, the distance parameter being a parameter describing a magnitude of a data difference between the source domain data and the target domain data;

determining, according to the training result and the image annotation, a loss function value corresponding to the source domain image; and training the neural network model to obtain a tissue nodule detection model by iteratively reducing a combination of the loss function value and the distance parameter.

A non-transitory computer-readable storage medium is provided, storing a computer program, the computer program, when executed by a processor, implementing the following operations:

obtaining a to-be-detected image;

inputting the to-be-detected image into a tissue nodule detection model, to obtain nodule location information, the tissue nodule detection model being obtained according to a tissue nodule detection model training apparatus, and the to-be-detected image and the target image having the same data structure, the tissue nodule detection model training apparatus including: a training data obtaining module, configured to obtain source domain data and target domain data, the source domain data including a source domain image and an image annotation, and the target domain data including a target image, the image annotation being used for indicating location information of a tissue nodule in the source domain image; a feature extraction and training module, configured to perform feature extraction on the source domain image through a neural network model to obtain a source domain sampling feature, perform feature extraction on the target image through the neural network model to obtain a target sampling feature, and determine a training result according to the source domain sampling feature; a distance parameter determining module, configured to determine a distance parameter between the source domain data and the target domain data according to the source domain sampling feature and the target sampling feature, the distance parameter being a parameter describing a magnitude of a data difference between the source domain data and the target domain data; a source domain loss determining module, configured to determine, according to the training result and the image annotation, a loss function value corresponding to the source domain image; and a model determining module, configured to train the neural network model to obtain a tissue nodule detection model by iteratively reducing a combination of the loss function value and the distance parameter.

A tissue nodule detection system is provided, including:

an image acquisition module, configured to acquire target domain data and a to-be-detected image;

a to-be-detected image obtaining module, configured to obtain the to-be-detected image acquired by the image acquisition module; and a detection model detection module, configured to input the to-be-detected image into a tissue nodule detection model, to obtain nodule location information, the tissue nodule detection model being obtained according to a tissue nodule detection model training apparatus, and the to-be-detected image and the target image having the same data structure, the tissue nodule detection model training apparatus including: a training data obtaining module, configured to obtain source domain data and the target domain data acquired by the image acquisition module, the source domain data including a source domain image and an image annotation, and the target domain data including a target image, the image annotation being used for indicating location information of a tissue nodule in the source domain image; a feature extraction and training module, configured to perform feature extraction on the source domain image through a neural network model to obtain a source domain sampling feature, perform feature extraction on the target image through the neural network model to obtain a target sampling feature, and determine a training result according to the source domain sampling feature; a distance parameter determining module, configured to determine a distance parameter between the source domain data and the target domain data according to the source domain sampling feature and the target sampling feature, the distance parameter being a parameter describing a magnitude of a data difference between the source domain data and the target domain data; a source domain loss determining module, configured to determine, according to the training result and the image annotation, a loss function value corresponding to the source domain image; and a model determining module, configured to train the neural network model to obtain a tissue nodule detection model by iteratively reducing a combination of the loss function value and the distance parameter.

According to the tissue nodule detection model training method and apparatus, the computer device, and the non-transitory storage medium, and the tissue nodule detection method and apparatus, the computer device, the non-transitory storage medium, and the system, a factor of the distance parameter between the source domain data and the target domain data is added during determining of a tissue nodule detection model. In this way, the difference between the sampling features of the source domain data and the target domain data that are extracted through the tissue nodule detection model can be reduced. Therefore, the detection accuracy can be improved by performing tissue nodule detection on data in the target domain through the tissue nodule detection model.

DESCRIPTION OF EMBODIMENTS

To make the objectives, technical solutions, and advantages of this application clearer and more comprehensible, this application is further described in detail with reference to the accompanying drawings and embodiments. It is to be understood that the specific embodiments described herein are only used for explaining this application, and are not used for limiting this application.

Figure 1:
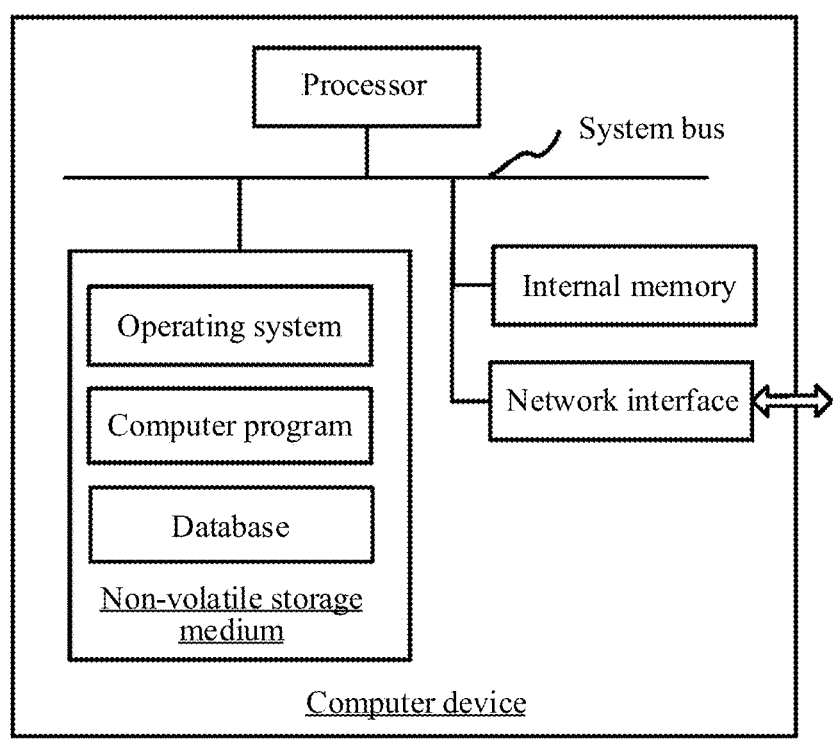
FIG. 1 is a diagram of an exemplary application environment of a tissue nodule detection model training method according to an embodiment.

FIG. 1 is a diagram of an exemplary application environment of a tissue nodule detection method and/or a tissue nodule detection model training method according to an embodiment. The tissue nodule detection method and/or the tissue nodule detection model training method may be applied to a computer-assisted cancer diagnostic system. As shown in FIG. 1, the tissue nodule detection method and/or the tissue nodule detection model training method is applied to a computer device. The computer device may be a terminal or a server. The terminal may be a desktop device or a mobile terminal. The server may be an independent physical server, a physical server cluster, or a virtual server. The computer device includes a processor, a memory, and a network interface connected through a system bus. The memory includes a non-transitory storage medium and an internal memory. The non-transitory storage medium of the computer device stores an operating system and a database, and the database stores source domain data and target domain data. The non-transitory storage medium of the computer device may further store a computer program, the computer program, when executed by a processor, may cause the processor to implement steps of the tissue nodule detection method and/or the tissue nodule detection model training method. The internal memory may further store a computer program, the computer program, when executed by a processor, may cause the processor to perform steps of the tissue nodule detection method and/or the tissue nodule detection model training method.

The computer device configured to perform the tissue nodule detection method and the computer device configured to perform the tissue nodule detection model training method may be different computer devices. For example, the computer device configured to perform the tissue nodule detection method may be a terminal, and the computer device configured to perform the tissue nodule detection model training method may be a server. For example, the server obtains a trained tissue nodule detection model by performing the tissue nodule detection model training method, and transmits the trained tissue nodule detection model to the terminal, and the terminal performs a tissue nodule detection task according to a to-be-detected image and the tissue nodule detection model.

Alternatively, the computer device configured to perform the tissue nodule detection method and the computer device configured to perform the tissue nodule detection model training method may be the same computer device. For example, the computer device configured to perform the tissue nodule detection method may also be a server. For example, the server obtains a trained tissue nodule detection model by performing the tissue nodule detection model training method, the terminal transmits a to-be-detected image to the server, and the server performs a tissue nodule detection task according to the to-be-detected image and the tissue nodule detection model, and feeds back a detection result to the terminal.

A person skilled in the art may understand that the structure shown in FIG. 1 is only a block diagram of a partial structure related to the solution of this application and does not constitute a limitation the computer device to which the solution of this application is applied. The computer device may specifically include more or fewer components than those shown in the figure, or some components may be combined, or a different component deployment may be used.

Figure 2:
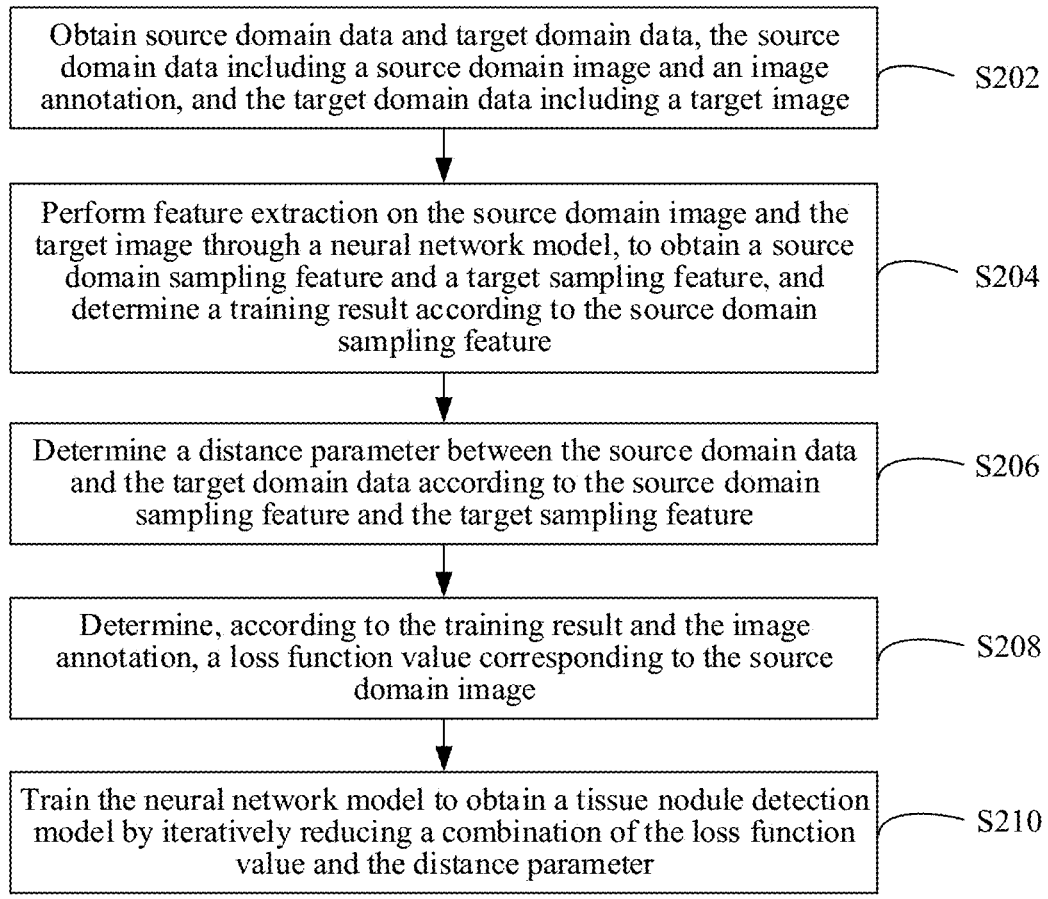
FIG. 2 is a schematic flowchart of a tissue nodule detection model training method according to an embodiment.

As shown in FIG. 2, in an embodiment, a tissue nodule detection model training method is provided. In this embodiment, description is made mainly by using an example in which the method is applied to the computer device in FIG. 1. The tissue nodule detection model training method includes the following steps:

S202. Obtain source domain data and target domain data, the source domain data including a source domain image and an image annotation, and the target domain data including a target image.

Optionally, an acquisition device of the source domain data and an acquisition device of a to-be-detected image are different. The to-be-detected image is an image on which tissue nodule detection needs to be performed. An acquisition device of the target domain data and the acquisition device of the to-be-detected image are the same. For example, when the to-be-detected image is a CT image acquired by a CT device of hospital A, the source domain data may be data obtained after a CT image randomly extracted from CT images acquired by CT devices in one city is annotated, and the target domain data may be a CT image acquired by the CT device of hospital A. In another example, when the to-be-detected image is a CT image acquired by a CT device of type B, the source domain data may be data obtained after a CT image randomly extracted from CT images acquired by CT devices of various types is annotated, and the target domain data may be a CT image acquired by the CT device of type B.

At least one of a sampling distance, a noise level, and a tissue nodule diameter distribution of the source domain image in the source domain data is different from that of the to-be-detected image. Sampling distances, noise levels, and tissue nodule diameter distributions of the target image in the target domain data and the to-be-detected image are the same. Whether two pieces of data are different or the same may be determined according to whether a discrepancy between the two pieces of data is within a preset threshold. For example, if a discrepancy between the sampling distances of the target image and the to-be-detected image is within the preset threshold, a discrepancy between the noise levels of the target image and the to-be-detected image is within the preset threshold, and a discrepancy between the tissue nodule diameter distributions of the target image and the to-be-detected image is within the preset threshold, the sampling distances, the noise levels, and the tissue nodule diameter distributions of the target image in the target domain data and the to-be-detected image are the same; otherwise, at least one of the sampling distance, the noise level, or the tissue nodule diameter distribution of the source domain image in the source domain data is different from that of the to-be-detected image. The preset threshold, may be set based on previous experience, and may be adjusted during the model training and deployment process.

An image annotation is used for indicating location information of a tissue nodule in the source domain image. The image annotation may be annotated in a manner of manual annotation, machine annotation, or may be annotated in a manner of man-machine combination. In this way, the accuracy of the image annotation is ensured. There is a correspondence between the image annotation and the source domain image.

To improve the model training efficiency, a ratio of the source domain image with at least one tissue nodule in the source domain data is not less than a preset value, where the preset value may be preset by a developer. For example, the preset value may be 50%, 80%, or 90%.

Because the tissue nodule is generally a three-dimensional structure, to further improve the detection accuracy, the source domain image and the target image may be three-dimensional images. For example, the source domain image and the target domain image may be cubical images of which a sampling size may be 128 dpi*128 dpi*5 dpi or 128 dpi*128 dpi*128 dpi.

S204. Perform feature extraction on the source domain image and the target image through a neural network model, to obtain a source domain sampling feature and a target sampling feature, and determine a training result according to the source domain sampling feature.

The computer device may perform feature extraction on the source domain image through a neural network model, to obtain a source domain sampling feature, and determine a training result according to the source domain sampling feature. The neural network model is a to-be-trained neural network model. The computer device performs feature extraction on each of the source domain images in the source domain data through the to-be-trained neural network model to obtain source domain sampling features, and determine training results according to the source domain sampling features. One source domain image may correspond to one source domain sampling feature and correspond to one training result. The training result is a result of location information of a tissue nodule in the source domain image obtained in the training process.

The computer device may perform feature extraction on the target image through the neural network model, to obtain a target sampling feature. For example, the computer device may perform feature extraction on each of the target images in the target domain data through the to-be-trained neural network model, to obtain target sampling features. One target image may correspond to one target sampling feature.

When the neural network model is initialized, an initial value may be assigned to a network parameter by using a Xavier initialization method. In the Xavier initialization method, to make information flow better in a network, the variance of the output of each layer should be as equal as possible. In this way, the model training efficiency may be improved.

S206. Determine a distance parameter between the source domain data and the target domain data according to the source domain sampling feature and the target sampling feature.

In a training batch, the source domain data includes a large quantity of source domain images, and the target domain data includes a large quantity of target images. The large quantity may mean that the quantity is greater than a preset value, such as 8, 20, 100, or 1000. The distance parameter is a parameter describing a magnitude of a data difference between two sets. In this embodiment, the distance parameter includes a parameter describing a magnitude of a data difference between the source domain data and the target domain data. For example, the distance parameter may be a magnitude based on a maximum mean distance, or may be a magnitude based on at least one of a Manhattan distance, a Euclidean distance, or a Chebyshev distance.

The computer device may determine the distance parameter between the source domain data and the target domain data according to the source domain sampling features of the source domain images in the source domain data and the target sampling features of the target images in the target domain data.

S208. Determine, according to the training result and the image annotation, a loss function value corresponding to the source domain image.

The computer device may determine, according to a difference between the training result and the image annotation, a loss function value corresponding to the source domain image. The loss function value may include a region loss function value based on a region extraction result, a classification loss function value based on a classification result, and a normalization loss function value based on a normalization result.

S210. Determine a tissue nodule detection model based on the loss function value, the distance parameter, and the neural network model.

The computer device may determine a neural network model when the loss function value and the distance parameter meet a preset condition as an optimal neural network model, and use the optimal neural network model in this case as the tissue nodule detection model. That is, the computer device use a network parameter corresponding to the neural network model when the loss function value and the distance parameter meet a preset condition as a network parameter of the tissue nodule detection model. In some implementations, the preset condition may include a preset threshold, and in order to meet the preset condition, the loss function value and the distance parameter need to be below their corresponding thresholds. It may be understood that, when the loss function value and the distance parameter do not meet the preset condition, the computer device iteratively updates the network parameter. For example, the computer device may use an adaptive optimizer such as an Adam optimizer to iteratively update the network parameter. The computer device goes back to step S202 and continues the training process until the training is completed, to determine the tissue nodule detection model.

The tissue may be a presentation of any human tissue such as a heart, a lung, a liver, a spleen, or a stomach tissue in a medical image.

The foregoing tissue nodule detection model training method includes: obtaining source domain data and target domain data, the source domain data including a source domain image and an image annotation, and the target domain data including a target image; performing feature extraction on the source domain image and the target image through a neural network model, to obtain a source domain sampling feature and a target sampling feature, and determining a training result according to the source domain sampling feature; determining a distance parameter between the source domain data and the target domain data according to the source domain sampling feature and the target sampling feature; determining, according to the training result and the image annotation, a loss function value corresponding to the source domain image; and determining a tissue nodule detection model based on the loss function value, the distance parameter, and the neural network model. According to the model training method, a factor of the distance parameter between the source domain data and the target domain data is added during determining of a tissue nodule detection model. In this way, the difference between the sampling features of the source domain data and the target domain data that are extracted by using the tissue nodule detection model can be reduced. Therefore, the detection accuracy can be improved by performing tissue nodule detection on data in the target domain by using the tissue nodule detection model.

The tissue nodule detection model is determined based on the loss function value corresponding to the source domain image, the distance parameter corresponding to the source domain data and the target domain data, and the neural network model. It can be seen that the entire process of determining the tissue nodule detection model does not need an image annotation of the target image. As such, no effort is needed to add annotation to the target image in the target domain data. In particular, only a one-time additional operation needs to be performed before the model training: acquiring existing target images in the target domain data, and enabling an execution device of this method to obtain the target domain data, for example, by inputting the target domain data to the execution device. In this way, the tissue nodule detection model training method based on this embodiment is simple in operation.

Optionally, based on the method of the foregoing embodiment, the objective of improving the detection accuracy may also be achieved without precluding the solution of annotating the target domain data.

In an embodiment, the distance parameter includes a discrepancy loss based on a maximum mean discrepancy (MMD), and the determining a distance parameter between the source domain data and the target domain data according to the source domain sampling feature and the target sampling feature in the embodiment shown in FIG. 2 includes: determining, by the computer device, the MMD-based discrepancy loss between the source domain data and the target domain data according to the source domain sampling feature and the target sampling feature.

Optionally, the MMD-based discrepancy loss is a parameter value based on the MMD, such as a square of the MMD, or the MMD.

The MMD-based discrepancy loss may be defined as an MMD between the source domain data and the target domain data, which may be represented as:

$$\text{MMD}(S,T) = \|E_{x\sim s}[\varphi(x)] - E_{y\sim T}[\varphi(y)]\|_{\mathcal{H}}$$

where $\varphi$ is a feature map that maps a feature from an original space where the source domain image and the target image are located to a reproducing kernel Hilbert space $\mathcal{H}$. In one batch of source domain data and target domain data, a distribution of the source domain sampling features of the source domain images in the source domain data may be an S-distribution, and a distribution of the target sampling features of the target images in the target domain data may be a T-distribution. E represents expectation, and a value of E may be a mean value of all elements.

To facilitate calculation, the MMD-based discrepancy loss may alternatively be defined as a form of an inner product of the reproducing kernel Hilbert space, namely, the square of the MMD. In this way, the model training efficiency can be improved. For example, in one embodiment, the square of the MMD may be represented as:

$$MMD^2(S,T) = \sum_{i=1}^{n_S}\sum_{j=1}^{n_S}\frac{k(z_i^S, z_j^S)}{n_S^2} + \sum_{i=1}^{n_T}\sum_{j=1}^{n_T}\frac{k(z_i^T, z_j^T)}{n_T^2} - 2\sum_{i=1}^{n_S}\sum_{j=1}^{n_T}\frac{k(z_i^S, z_j^T)}{n_S n_T}$$

where k is a kernel function and used for representing a mapping relationship between features, $n_S$ is a quantity of the source domain images in the source domain data, and $n_T$ is a quantity of the target images in the target domain data.

In an embodiment, determining a MMD-based discrepancy loss between the source domain data and the target domain data according to the source domain sampling feature and the target sampling feature includes: determining, by the computer device, based on a Gaussian kernel function, a MMD-based discrepancy loss between the source domain data and the target domain data according to the source domain sampling feature and the target sampling feature.

During determining of the MMD-based discrepancy loss, the kernel function may adopt a Gaussian kernel function. In this way, the accuracy of the MMD-based discrepancy loss can be improved, to further reduce the difference between the sampling features of the source domain data and the target domain data. Therefore, the detection accuracy may be further improved.

In an embodiment, the MMD-based discrepancy loss may alternatively be defined as a form of an inner product of the reproducing kernel Hilbert space, namely, the square of the MMD. The square of the MMD may be represented by using the foregoing formula, and the kernel function k may specifically be a Gaussian kernel function, which may be represented as:

$$k(x,y)=e^{-\|x-y\|^2/b}$$

where b is a bandwidth parameter. The bandwidth parameter may be adjusted according to experience before the training. e is the natural constant.

Figure 3:
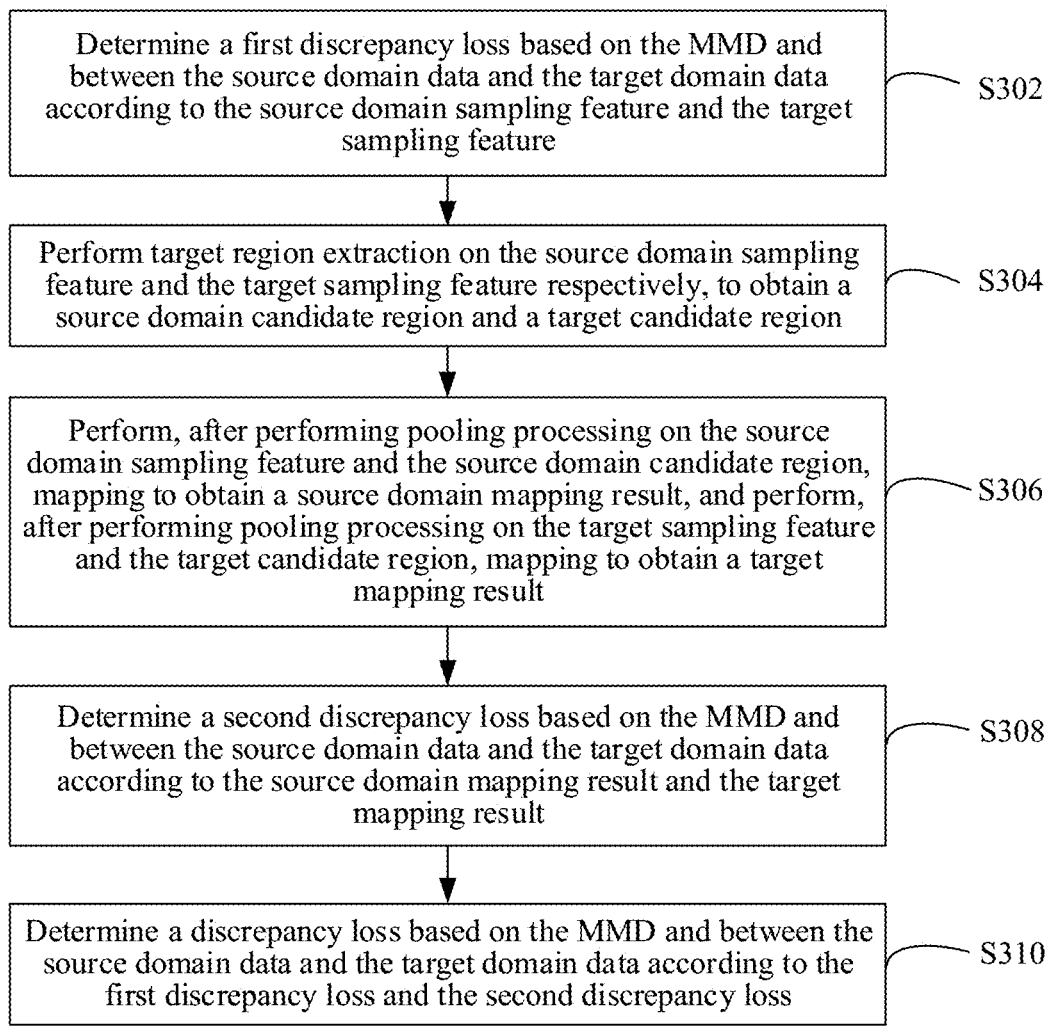
FIG. 3 is a schematic flowchart of one step of the tissue nodule detection model training method in FIG. 2.

As shown in FIG. 3, in an embodiment, the determining a MMD-based discrepancy loss between the source domain data and the target domain data according to the source domain sampling feature and the target sampling feature may include the following steps:

S302. Determine a first MMD-based discrepancy loss between the source domain data and the target domain data according to the source domain sampling feature and the target sampling feature. The first MMD-based discrepancy loss is determined based on the source domain sampling feature and the target sampling feature.

S304. Perform target region extraction on the source domain sampling feature and the target sampling feature, respectively, to obtain a source domain candidate region and a target candidate region.

The computer device may perform target region extraction on the source domain sampling feature through the neural network model, to obtain a source domain candidate region; and perform target region extraction on the target sampling feature through the neural network model, to obtain a target candidate region.

S306. Perform, after performing pooling processing on the source domain sampling feature and the source domain candidate region, mapping to obtain a source domain mapping result, and perform, after performing pooling processing on the target sampling feature and the target candidate region, mapping to obtain a target mapping result.

The computer device may perform, after performing pooling processing on the source domain sampling feature and the source domain candidate region through the neural network model, mapping to obtain a source domain mapping result, and perform, after performing pooling processing on the target sampling feature and the target candidate region through the neural network model, mapping to obtain a target mapping result.

S308. Determine a second MMD-based discrepancy loss between the source domain data and the target domain data according to the source domain mapping result and the target mapping result. A second MMD-based discrepancy loss is determined based on the source domain mapping result and the target mapping result.

S310. Determine a MMD-based discrepancy loss between the source domain data and the target domain data according to the first MMD-based discrepancy loss and the second MMD-based discrepancy loss.

In this embodiment, when the first MMD-based discrepancy loss is determined, inputs of the kernel function are the source domain sampling feature corresponding to the source domain data and the target sampling feature corresponding to the target domain data. When the second MMD-based discrepancy loss is determined, inputs of the kernel function are the source domain mapping result corresponding to the source domain data and the target mapping result corresponding to the target domain data. When determining the MMD-based discrepancy loss between the source domain data and the target domain data according to the first MMD-based discrepancy loss and the second MMD-based discrepancy loss, the computer device may perform processing on the first MMD-based discrepancy loss and the second MMD-based discrepancy loss based on a preset rule, to obtain the MMD-based discrepancy loss between the source domain data and the target domain data. For example, a weighted sum of the first MMD-based discrepancy loss and the second MMD-based discrepancy loss may be calculated, to obtain the MMD-based discrepancy loss.

Based on the model training method of this embodiment, after feature extraction and full connected mapping are performed, the first MMD-based discrepancy loss and the second MMD-based discrepancy loss may be respectively obtained. In this way, the difference between the source domain data and the target domain data may be further reduced. Therefore, the detection accuracy may be further improved by performing tissue nodule detection on data in the target domain using the tissue nodule detection model.

Figure 4:
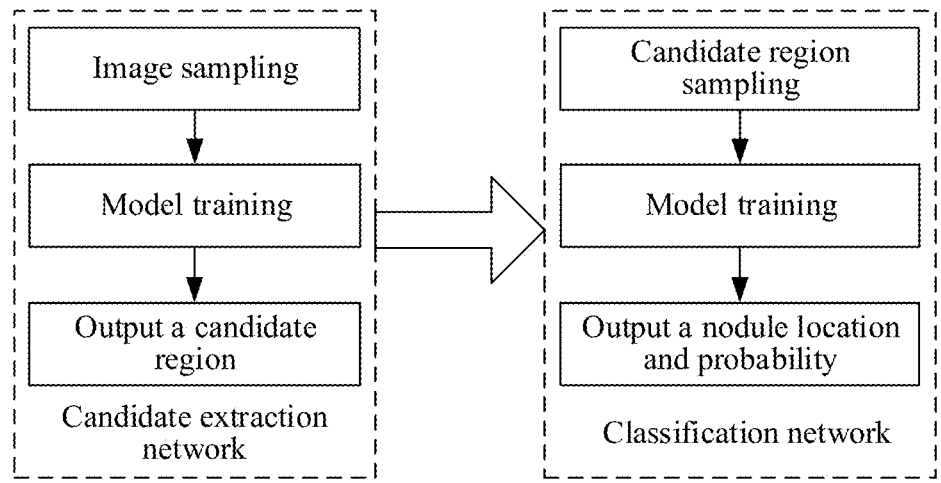
FIG. 4 is a schematic diagram of a working principle of a tissue nodule detection model training method according to an embodiment.

In an embodiment, the tissue nodule detection model may be a lung nodule detection model. As shown in FIG. 4, a neural network model in a training process includes a candidate extraction network and a classification network. The computer device may perform feature extraction on the source domain image and the target image through the candidate extraction network, to obtain a source domain sampling feature and a target sampling feature. The computer device performs target region extraction on the source domain sampling feature and the target sampling feature respectively through the candidate extraction network, to obtain a source domain candidate region and a target candidate region. A network structure in which low-level features and high-level features are combined may be selected as the candidate extraction network. For example, the candidate extraction network may be a three-dimensional convolutional neural network (3D CNN) structure, such as a three-dimensional edge detection convolutional neural network (3D U-Net) model or a three-dimensional feature pyramid network (3D FPN) model. In this case, a cubic region sampled by a three-dimensional CT image is inputted, and coordinates and a diameter of a lung nodule candidate location in the cubic region are outputted. A smaller value may be set for a detection threshold of the candidate extraction network, to ensure a lower rate of missed detection.

To filter out a false positive detection result generated by the candidate extraction network and improve the detection accuracy, further classification may be performed on the extracted candidate locations through the classification network based on the candidate extraction network. Mapping may be performed to obtain a source domain mapping result through the classification network after pooling processing is performed on the source domain sampling feature and the source domain candidate region, and mapping may be performed to obtain a target mapping result after pooling processing is performed on the target sampling feature and the target candidate region. For example, the classification network may extract a smaller cubic picture centered on the candidate location as an input, output a probability that the candidate region is true positive, and slightly adjust the coordinates of the candidate lung nodule.

Figure 5:
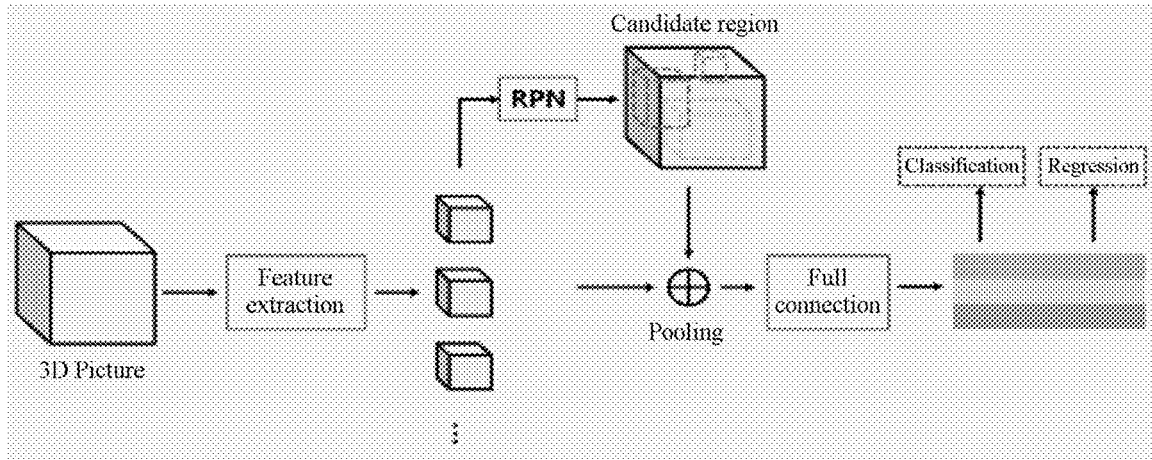
FIG. 5 is a schematic diagram of a working principle of a tissue nodule detection model training method according to another embodiment.

In an embodiment, as shown in FIG. 5, the neural network model in the training process may be a three-dimensional faster region convolutional neural network (3D Faster RCNN). A network structure of the 3D Faster RCNN includes a 3D region proposal network (RPN) branch and a classification regression branch. After obtaining a source domain sampling feature and a target sampling feature by performing feature extraction on a source domain image and a target image through a feature extraction network based on a CNN, the computer device performs target region extraction on the source domain sampling feature and the target sampling feature through the RPN branch to obtain a source domain candidate region and a target candidate region, respectively. The computer device performs mapping to obtain a source domain mapping result after performing pooling processing on the source domain sampling feature and the source domain candidate region through the classification regression branch, and performs mapping to obtain a target mapping result after performing pooling processing on the target sampling feature and the target candidate region. It may be understood that, the two branches share sampling features extracted by the feature extraction network based on the CNN. The 3D RPN branch outputs a region most likely being a region for the detection target, and extracts a feature of this region by using a pooling layer for the classification regression branch to learn a probability that this region is a lung nodule and coordinates of this region.

In an embodiment, the step of determining a tissue nodule detection model based on the loss function value, the distance parameter, and the neural network model includes: determining, by the computer device, a modified loss function value based on the loss function value and the distance parameter; and determining the tissue nodule detection model based on the total loss function value and the neural network model. In some implementations, for example, the modification to the loss function value may include an addition operation (summation) on the loss function value and the distance parameter. In this case, the modified loss function value may also be considered as a total loss function value. In other implementations, for example, other types of operations such as a multiplication operation may also be considered.

The total loss function value is a value determining whether the neural network model reaches an optimal loss function in a process of training the neural network model. The total loss function value is determined based on the loss function value corresponding to the source domain image and the distance parameter between the source domain data and the target domain data. In this way, the distance parameter is used as an impact factor affecting the loss function value, so that the difference between the sampling features of the source domain data and the target domain data can be reduced in the process of training the tissue nodule detection model. Therefore, the detection accuracy can be improved by performing tissue nodule detection on data in the target domain by using the tissue nodule detection model.

When the total loss function value converges, a neural network model is determined as an optimal neural network model and the optimal neural network is used as the tissue nodule detection model. That is, a network parameter corresponding to the neural network model when the total loss function value converges is used as a network parameter of the tissue nodule detection model. Further, if the total loss function value converges in a preset time, a neural network model may be used as the tissue nodule detection model. Otherwise if the total loss function value does not converge in the preset time, a neural network model when the preset time arrives may be used as the tissue nodule detection model. The preset time may be a time when a training time reaches a preset value, or may be a time when a quantity of times of iterative update reaches a preset value in the training process.

In an embodiment, the distance parameter includes a square of the MMD; and the step of determining a total loss function value according to the loss function value and the distance parameter includes: performing, by the computer device, linear summation on the square of the MMD and the loss function value, to obtain the total loss function value.

The linear summation refers to performing summation after multiplying each to-be-added data by a preset coefficient. The loss function value may include a region loss function value based on a region extraction result, a classification loss function value based on a classification result, and a normalization loss function value based on a normalization result. In this embodiment, the total loss function value may be obtained in a manner of performing linear summation on the square of the MMD and the loss function value. In this way, the calculation amount may be reduced and the model training efficiency may be improved.

In an embodiment, the total loss function value may be represented as:

$$L = L_{RPN} + L_{Cls} + L_{Reg} + \lambda \text{MMD}^2(S, T)$$

where $L_{RPN}$ is the region loss function value based on a region extraction result, $L_{Cls}$ is the classification loss function value based on a classification result, $L_{Reg}$ is the normalization loss function value based on a normalization result, and $\text{MMD}^2(S, T)$ is a square of the MMD between the source domain data and the target domain data. $\lambda$ is a hyperparameter and may be adjusted according to experience before the training.

In an embodiment, the step of performing feature extraction on the source domain image and the target image through a neural network model to obtain a source domain sampling feature and a target sampling feature includes: segmenting, by the computer device, the source domain image and the target image, to obtain a source domain tissue region and a target tissue region, respectively; and performing feature extraction on the source domain tissue region and the target tissue region through the neural network model, to obtain the source domain sampling feature and the target sampling feature.

In one implementation, segmentation (or cropping) is to cut off non-tissue region in the image, and reserve the tissue region in the image. The computer device segments the source domain image to obtain the source domain tissue region and segments the target image to obtain the target tissue region. In this way, pre-processing is performed on the source domain image and the target image. In an embodiment, the computer device may first scale a pixel value in the source domain image into a region of 0-1, and then crop the source domain tissue region, such as a source domain lung region. Accordingly, the computer device may first scale a pixel value in the target image to a region of 0-1, and then crop the target tissue region, such as a target lung region. In this way, the calculation can be facilitated so as to improve the model training efficiency.

Based on the model training method of this embodiment, the computer device segments the source domain image and the target image, removes edge parts of the tissue region, and then performs feature extraction based on a segmented result. In this way, interference is reduced, and the model accuracy can be further improved.

In an embodiment, as shown in FIG. 4, the computer device may segment, by using the candidate extraction network of the neural network model, the source domain image to obtain the source domain tissue region, and segment the target image to obtain the target tissue region.

In an embodiment, segmenting the source domain image and the target image to obtain a source domain tissue region and a target tissue region respectively includes: segmenting, by the computer device, the source domain image and the target image respectively, to obtain a source domain lung region and a target lung region, respectively. Lung nodule detection is one important component in the computer-assisted lung cancer diagnostic system. A lung nodule detected from a lung CT image is an important reference for early screening and diagnosis of a lung cancer. Based on the method of this embodiment, the tissue nodule detection model training method is applied to lung nodule detection model training, and an intermediate layer of the neural network model may output consistent features in response to images with different distributions (source domain data and target domain data) by introducing a domain adaptation technology into the lung nodule detection. Subsequently, consistent detection results may be given to the images with different distributions based on the consistent features. In this way, the accuracy of the lung nodule detection on the target image is improved, and a more reliable assisted diagnosis result is finally given.

In an embodiment, the source domain image in the source domain data and the target image in the target domain data meet a quantity relationship. The quantity relationship may be that a ratio of a quantity of the source domain images to a quantity of the target images is a preset value. The preset value is not greater than a threshold, and the threshold may be 10, 5, 2, 1, or the like. In this way, by ensuring the quantity relationship between the target images and the source domain images, the impact of the factor of the distance parameter between the source domain data and the target domain data is ensured during determining of a tissue nodule detection model. Therefore, the detection accuracy is improved.

In an embodiment, the quantity of the source domain images in the source domain data is equal to the quantity of the target images in the target domain data. That is, the ratio of the quantity of the source domain images to the quantity of the target images is 1, namely, the preset value is 1. In this way, by ensuring the equal quantity relationship between the target images and the source domain images, greater impact of the factor of the distance parameter between the source domain data and the target domain data is ensured during determining of a tissue nodule detection model. Therefore, the detection accuracy is improved.

In an embodiment, performing feature extraction on the source domain image and the target image through a neural network model, to obtain a source domain sampling feature and a target sampling feature, and determining a training result according to the source domain sampling feature includes: performing, by the computer device, feature extraction on the source domain image through a first neural network model, to obtain the source domain sampling feature, and determining a training result according to the source domain sampling feature; and performing feature extraction on the target image through a second neural network model, to obtain the target sampling feature, a second neural network and a first neural network sharing a same weight.

Sharing a same weight means that network parameters of the first neural network and the second neural network are shared. The network parameters of the two networks may be implemented as being stored in one location, or may be implemented as that when a network parameter of the two networks are synchronized. In this way, it is ensured that the network parameters of the first neural network and the second neural network are always consistent, and the two neural networks may be enabled to work simultaneously, thereby improving the model training efficiency.

Figure 6:
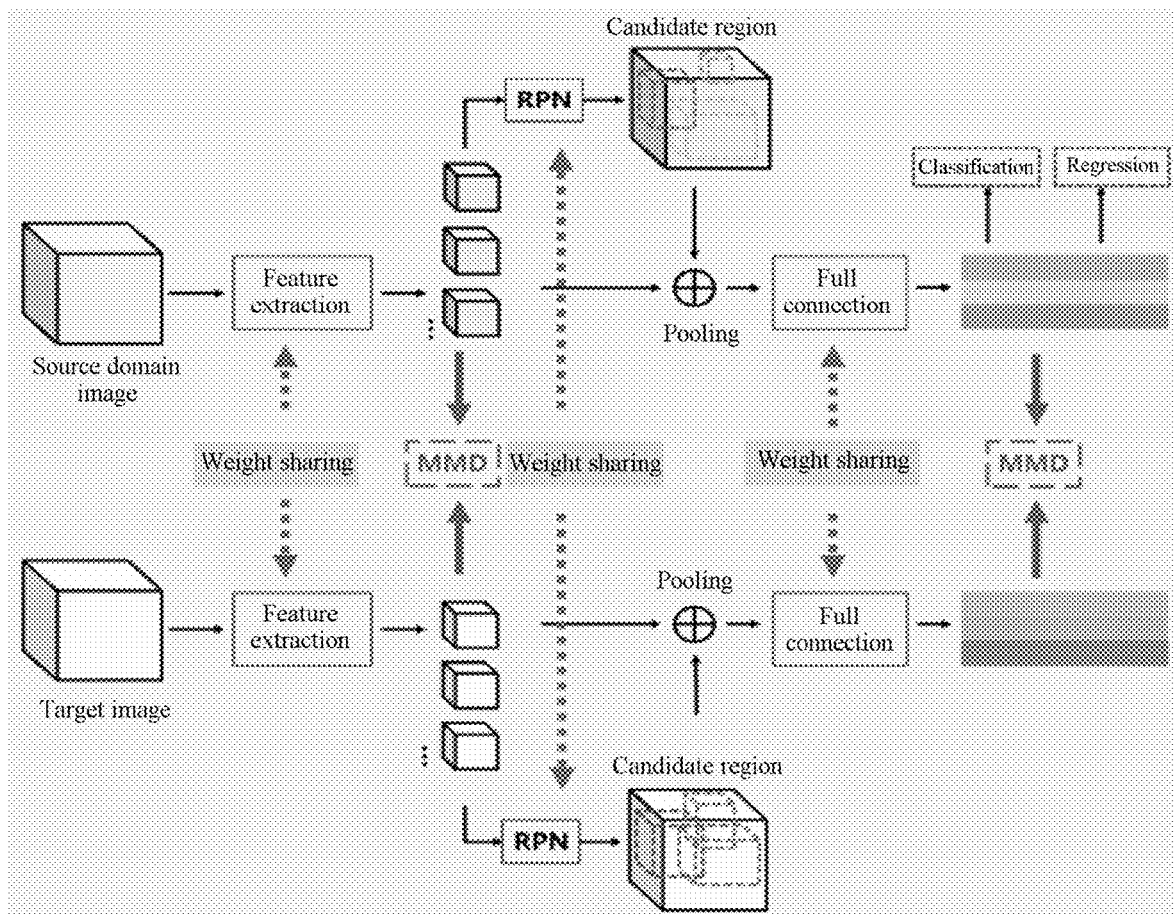
FIG. 6 is a schematic diagram of a working principle of a tissue nodule detection model training method according to still another embodiment.

In an embodiment, as shown in FIG. 6, the neural network model adopted in the training process may be a 3D Faster RCNN. In each batch of training data of a network, training data samples include source domain data from a source domain and target domain data from a target domain. The source domain refers to a picture distribution in an original dataset, and the target domain refers to a picture distribution in an actual deployment scenario of a detection algorithm. Generally, the two distributions are remarkably different. Source domain images in the source domain have image annotation, and the image annotation is used for describing location information, such as coordinates and a diameter of a tissue nodule in the source domain image; conversely, images in the target domain do not have any annotation. That is, the source domain data includes source domain images with annotation, and the target domain data includes target images with no annotation. Using a Faster RCNN algorithm, an output of a source domain image with an annotation may include a region loss function value based on a region extraction result, a classification loss function value based on a classification result, and a normalization loss function value based on a normalization result. A target image with no annotation is used for being inputted into forward propagation of the neural network to generate a target sampling feature. In this embodiment, a loss function based on the MMD, that is, a discrepancy loss, is respectively added to two locations of the 3D Faster RCNN. The first location is a previous layer of a region feature extraction network, that is, a feature extraction network layer; and the second location is a previous layer of classification regression, that is, a fully connected layer. The loss function based on the MMD is used for minimizing a discrepancy between the two distributions by adding the MMD-based discrepancy loss to the training of the 3D Faster RCNN. The loss function based on the MMD is added to the first location, that is, a first MMD-based discrepancy loss between the source domain data and the target domain data is determined according to the source domain sampling feature and the target sampling feature, so that features extracted by the 3D Faster RCNN from the inputted source domain image and the target image are consistent. Therefore, the source domain sampling feature extracted from the source domain image and the target sampling feature extracted from the target image in the network have similar distributions when performing detection. The loss function based on the MMD is added to a second location, that is, a second MMD-based discrepancy loss between the source domain data and the target domain data is determined according to the source domain mapping result and the target mapping result, so that extracted features of the source domain candidate region and the target candidate region in the network are consistent. Neural networks obtained by performing training on the consistent features of the source domain and the target domain also have the consistency between the source domain and the target domain. In this way, generalization of a model in the target domain can be increased, thereby improving the detection accuracy.

In this embodiment, as shown in FIG. 6, the first neural network model at the upper part and the second neural network model at the lower part have the same structure, and receive images of the source domain and the target domain as inputs, respectively, to generate a corresponding distance parameter according to a shared network parameter. Since the target image has no annotation, the second neural network model does not generate a loss function value based on the target domain data.

In this embodiment, performance of the tissue nodule detection model on to-be-detected images with different distributions from source domain data is improved through the domain adaptation technology. Based on the 3D Faster RCNN detection algorithm, when a CNN is trained by using the source domain data, target domain data with no annotation is added to this training batch for forward propagation, and an MMD-based discrepancy loss is added to the RPN layer and the full connected layer, to minimize a distance between the feature distribution of the source domain data and the feature distribution of the target domain data. In this way, an intermediate layer of the CNN is able to extract consistent sampling features from the source domain data and the target domain data while the model obtains a detection capability and gives consistent detection results, thereby improving the detection accuracy. Meanwhile, as long as a target domain image with no annotation is provided, detection performance of the model on images with different distributions may be improved, to improve the reliability of the assisted diagnosis result.

In an embodiment, a tissue nodule detection model training method is provided, including:

obtaining source domain data and target domain data, the source domain data including a source domain image and an image annotation, and the target domain data including a target image, the source domain image in the source domain data and the target image in the target domain data being equal in quantity;

segmenting the source domain image and the target image respectively, to obtain a source domain tissue region and a target tissue region;

performing feature extraction on the source domain tissue region through a first neural network model, to obtain a source domain sampling feature, and determining a training result according to the source domain sampling feature;

performing feature extraction on the target tissue region through a second neural network model, to obtain a target sampling feature, a second neural network and a first neural network sharing a same weight;

determining, based on a Gaussian kernel function, a first MMD-based discrepancy loss between the source domain data and the target domain data according to the source domain sampling feature and the target sampling feature;

performing target region extraction on the source domain sampling feature and the target sampling feature respectively, to obtain a source domain candidate region and a target candidate region;

performing, after performing pooling processing on the source domain sampling feature and the source domain candidate region, mapping to obtain a source domain mapping result, and performing, after performing pooling processing on the target sampling feature and the target candidate region, mapping to obtain a target mapping result;

determining, based on the Gaussian kernel function, a second MMD-based discrepancy loss between the source domain data and the target domain data according to the source domain mapping result and the target mapping result;

determining a square of the MMD between the source domain data and the target domain data according to the first MMD-based discrepancy loss and the second MMD-based discrepancy loss;

determining, according to the training result and the image annotation, a loss function value corresponding to the source domain image;

performing linear summation on the square of the MMD and the loss function value, to obtain a total loss function value; and determining a tissue nodule detection model based on the total loss function value and the neural network models.

Figure 7:
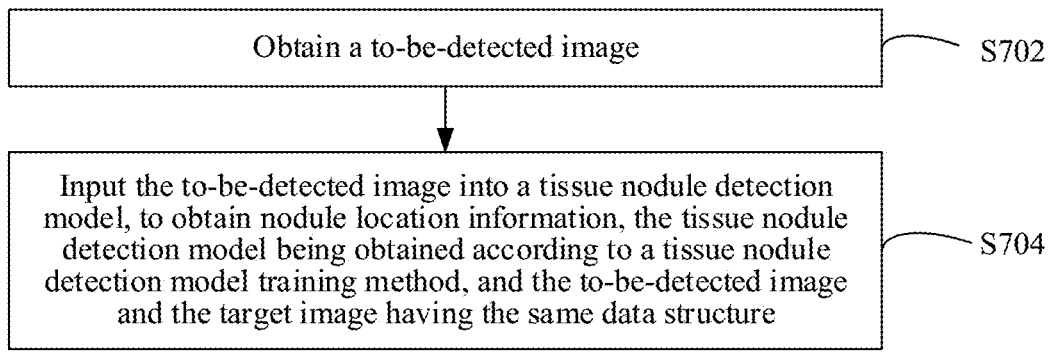
FIG. 7 is a schematic flowchart of a tissue nodule detection method according to an embodiment.

As shown in FIG. 7, in an embodiment, a tissue nodule detection method corresponding to the tissue nodule detection model training method is provided. In this embodiment, description is mainly made by using an example in which the method is applied to the computer device in FIG. 1. The tissue nodule detection method includes the following steps:

S702. Obtain a to-be-detected image.

S704. Input the to-be-detected image into a tissue nodule detection model, to obtain nodule location information, the tissue nodule detection model being obtained according to a tissue nodule detection model training apparatus, and the to-be-detected image and the target image being taken under comparable conditions and having a same data structure. For example, both the images have a same data structure indicative of color, brightness, contrast, shape, or the like.

For example, the tissue nodule detection model training apparatus includes: a training data obtaining module, configured to obtain source domain data and target domain data, the source domain data including a source domain image and an image annotation, and the target domain data including a target image, the image annotation being used for indicating location information of a tissue nodule in the source domain image; a feature extraction and training module, configured to perform feature extraction on the source domain image through a neural network model to obtain a source domain sampling feature, perform feature extraction on the target image through the neural network model to obtain a target sampling feature, and determine a training result according to the source domain sampling feature; a distance parameter determining module, configured to determine a distance parameter between the source domain data and the target domain data according to the source domain sampling feature and the target sampling feature, the distance parameter being a parameter describing a magnitude of a data difference between the source domain data and the target domain data; a source domain loss determining module, configured to determine, according to the training result and the image annotation, a loss function value corresponding to the source domain image; and a model determining module, configured to determine a tissue nodule detection model based on the loss function value, the distance parameter, and the neural network model.

The to-be-detected image is an image on which tissue region detection is to be performed. It may be understood that the to-be-detected image belongs to a target domain.

The tissue nodule detection model may reduce the difference between the extracted sampling features of the source domain data and the target domain data. Therefore, the detection accuracy can be improved by performing tissue nodule detection on data in the target domain by using the tissue nodule detection model.

As long as target domain data with no annotation is provided, a tissue nodule detection model consistent for a tissue CT scanning imaging condition may be trained. The user only needs to perform a one-time addition interaction to upload tissue scanning image data generated by a local CT instrument, to be used as target domain data. The user does not need to manually annotate the local CT images. By using the tissue nodule detection model trained according to the domain adaptation method, a higher detection rate of a tissue nodule and a lower false detection rate can be obtained from the target domain data of which the distribution is different from that of the source domain data with an annotation, thereby improving the reliability and flexibility of a computer-assisted tissue canceration diagnostic system.

Meanwhile, based on the tissue nodule detection method of this embodiment, the accuracy and reliability of tissue nodule detection can be improved while being almost transparent to the user (doctor), and this method does not conflict with an existing user habit and experience formed on a previous-generation product, thus ensuring a smooth transition process to the new detection model.

It is to be understood that, although the steps in the flowcharts of FIG. 2, FIG. 3, and FIG. 7 are sequentially displayed according to indication of arrows, the steps are not necessarily sequentially performed in the sequence indicated by the arrows. Unless explicitly specified in this specification, execution of the steps is not strictly limited in the sequence, and the steps may be performed in other sequences. In addition, at least some steps in FIG. 2, FIG. 3, and FIG. 7 may include a plurality of sub-steps or a plurality of stages. The sub-steps or the stages are not necessarily performed at the same moment, and instead may be performed at different moments. The sub-steps or the stages are not necessarily performed sequentially, and instead may be performed in turn or alternately with another step or at least some of sub-steps or stages of the other step.

Figure 8:
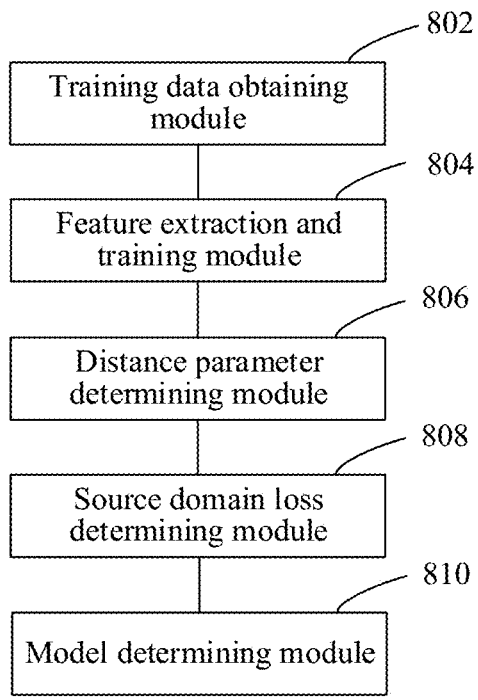
FIG. 8 is a structural block diagram of a tissue nodule detection model training apparatus according to an embodiment.

In an embodiment, as shown in FIG. 8, a tissue nodule detection model training apparatus run on the computer device in FIG. 1 is provided, including:

a training data obtaining module 802, configured to obtain source domain data and target domain data, the source domain data including a source domain image and an image annotation, and the target domain data including a target image, the image annotation being used for indicating location information of a tissue nodule in the source domain image;

a feature extraction and training module 804, configured to perform feature extraction on the source domain image through a neural network model to obtain a source domain sampling feature, perform feature extraction on the target image through the neural network model to obtain a target sampling feature, and determine a training result according to the source domain sampling feature;

a distance parameter determining module 806, configured to determine a distance parameter between the source domain data and the target domain data according to the source domain sampling feature and the target sampling feature, the distance parameter being a parameter describing a magnitude of a data difference between the source domain data and the target domain data;

a source domain loss determining module 808, configured to determine, according to the training result and the image annotation, a loss function value corresponding to the source domain image; and a model determining module 810, configured to determine a tissue nodule detection model based on the loss function value, the distance parameter, and the neural network model.

According to the tissue nodule detection model training apparatus, a factor of the distance parameter between the source domain data and the target domain data is introduced during determining of a tissue nodule detection model. In this way, the difference between the sampling features of the source domain data and the target domain data that are extracted by using the tissue nodule detection model can be reduced. Therefore, the detection accuracy can be improved by performing tissue nodule detection on data in the target domain by using the tissue nodule detection model.

In an embodiment, the distance parameter includes a discrepancy loss based on an MMD; and the distance parameter determining module is configured to determine the MMD-based discrepancy loss between the source domain data and the target domain data according to the source domain sampling feature and the target sampling feature.

In an embodiment, the distance parameter determining module is configured to determine, based on a Gaussian kernel function, the discrepancy loss based on a MMD and between the source domain data and the target domain data according to the source domain sampling feature and the target sampling feature.

In an embodiment, the distance parameter determining module includes:

a first discrepancy loss unit, configured to determine a first MMD-based discrepancy loss between the source domain data and the target domain data according to the source domain sampling feature and the target sampling feature;

a candidate region determining unit, configured to perform target region extraction on the source domain sampling feature, to obtain a source domain candidate region, and perform target region extraction on the target sampling feature, to obtain a target candidate region;

a mapping result determining unit, configured to perform, after performing pooling processing on the source domain sampling feature and the source domain candidate region, mapping to obtain a source domain mapping result, and perform, after performing pooling processing on the target sampling feature and the target candidate region, mapping to obtain a target mapping result;

a second discrepancy loss unit, configured to determine a second MMD-based discrepancy loss between the source domain data and the target domain data according to the source domain mapping result and the target mapping result; and a comprehensive discrepancy determining unit, configured to determine the MMD-based discrepancy loss between the source domain data and the target domain data according to the first MMD-based discrepancy loss and the second MMD-based discrepancy loss.

In an embodiment, the apparatus further includes a total loss determining module, where the total loss determining module is configured to determine a total loss function value according to the loss function value and the distance parameter; and the model determining module is further configured to determine the tissue nodule detection model based on the total loss function value and the neural network model.

In an embodiment, the distance parameter includes a square of the MMD; and the total loss determining module is configured to perform linear summation on the square of the MMD and the loss function value, to obtain the total loss function value.

In an embodiment, the apparatus further includes a tissue region segmentation module, where the tissue region segmentation module is configured to segment the source domain image, to obtain a source domain tissue region, and segment the target image, to obtain a target tissue region; and the feature extraction and training module is configured to perform feature extraction on the source domain tissue region through the neural network model, to obtain the source domain sampling feature, and perform feature extraction on the target tissue region through the neural network model, to obtain the target sampling feature.

In an embodiment, the source domain image in the source domain data and the target image in the target domain data meet a quantity relationship.

In an implementation, the source domain image in the source domain data and the target image in the target domain data are equal in quantity.

In an embodiment, the feature extraction and training module includes:

a feature extraction and training unit, configured to perform feature extraction on the source domain image through a first neural network model, to obtain the source domain sampling feature, and determine the training result according to the source domain sampling feature; and a feature extraction unit, configured to perform feature extraction on the target image through a second neural network model, to obtain the target sampling feature, a second neural network and a first neural network sharing a same weight.

Figure 9:
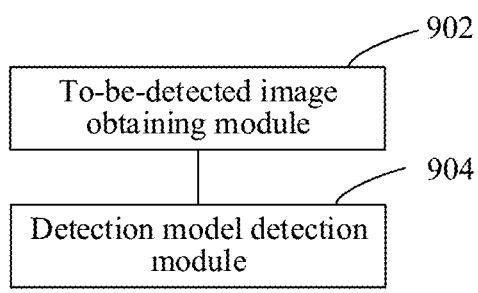
FIG. 9 is a structural block diagram of a tissue nodule detection apparatus according to an embodiment.

In an embodiment, as shown in FIG. 9, a tissue nodule detection apparatus run on the computer device in FIG. 1 and corresponding to the tissue nodule detection model training method is provided, including:

a to-be-detected image obtaining module 902, configured to obtain a to-be-detected image; and a detection model detection module 904, configured to input the to-be-detected image into a tissue nodule detection model, to obtain nodule location information, the tissue nodule detection model being obtained according to the tissue nodule detection model training apparatus, and the to-be-detected image and the target image having the same data structure, For example, the tissue nodule detection model training apparatus includes: a training data obtaining module, configured to obtain source domain data and target domain data, the source domain data including a source domain image and an image annotation, and the target domain data including a target image, the image annotation being used for indicating location information of a tissue nodule in the source domain image; a feature extraction and training module, configured to perform feature extraction on the source domain image through a neural network model to obtain a source domain sampling feature, perform feature extraction on the target image through the neural network model to obtain a target sampling feature, and determine a training result according to the source domain sampling feature; a distance parameter determining module, configured to determine a distance parameter between the source domain data and the target domain data according to the source domain sampling feature and the target sampling feature, the distance parameter being a parameter describing a magnitude of a data difference between the source domain data and the target domain data; a source domain loss determining module, configured to determine, according to the training result and the image annotation, a loss function value corresponding to the source domain image; and a model determining module, configured to determine a tissue nodule detection model based on the loss function value, the distance parameter, and the neural network model.

The to-be-detected image is an image on which tissue region detection is to be performed. It may be understood that the to-be-detected image belongs to a target domain. The tissue nodule detection model may reduce the difference between the extracted sampling features of the source domain data and the target domain data. Therefore, the detection accuracy can be improved by performing tissue nodule detection on data in the target domain by using the tissue nodule detection model.

In an embodiment, a computer device is provided. The computer device may be a server, and an internal structure diagram thereof may be shown in FIG. 1. The computer device includes a memory and a processor, the memory storing a computer program, and the processor, when executing the computer program, implementing steps of the tissue nodule detection model training method and/or the tissue nodule detection method.

In an embodiment, a computer-readable storage medium is provided, storing a computer program, the computer program, when executed by a processor, implementing steps of the tissue nodule detection model training method and/or the tissue nodule detection method.

In an embodiment, a tissue nodule detection system corresponding to the tissue nodule detection method and apparatus is provided, including:

an image acquisition module, configured to acquire target domain data and a to-be-detected image;

a to-be-detected image obtaining module, configured to obtain the to-be-detected image acquired by the image acquisition module; and a detection model detection module, configured to input the to-be-detected image into a tissue nodule detection model, to obtain nodule location information, the tissue nodule detection model being obtained according to a tissue nodule detection model training apparatus, and the to-be-detected image and the target image having the same data structure, the tissue nodule detection model training apparatus including: a training data obtaining module, configured to obtain source domain data and the target domain data acquired by the image acquisition module, the source domain data including a source domain image and an image annotation, and the target domain data including a target image; the image annotation being used for indicating location information of a tissue nodule in the source domain image; a feature extraction and training module, configured to perform feature extraction on the source domain image through a neural network model to obtain a source domain sampling feature, perform feature extraction on the target image through the neural network model to obtain a target sampling feature, and determine a training result according to the source domain sampling feature; a distance parameter determining module, configured to determine a distance parameter between the source domain data and the target domain data according to the source domain sampling feature and the target sampling feature, the distance parameter being a parameter describing a magnitude of a data difference between the source domain data and the target domain data; a source domain loss determining module, configured to determine, according to the training result and the image annotation, a loss function value corresponding to the source domain image; and a model determining module, configured to determine a tissue nodule detection model based on the loss function value, the distance parameter, and the neural network model.

It may be understood that, the image acquisition module, the to-be-detected image obtaining module, and the detection model detection module may be stored in a memory of one device, that is, the steps of acquiring target domain data and a to-be-detected image, obtaining the to-be-detected image acquired by the image acquisition module, and inputting the to-be-detected image into a tissue nodule detection model, to obtain nodule location information may be performed by using the device. The image acquisition module, the to-be-detected image obtaining module, and the detection model detection module may alternatively be stored in memories of different devices, and the steps of acquiring target domain data and a to-be-detected image, obtaining the to-be-detected image acquired by the image acquisition module, and inputting the to-be-detected image into a tissue nodule detection model, to obtain nodule location information may be performed by using different devices. For example, the step of acquiring target domain data and a to-be-detected image may be performed by using one device or devices of one type, and the steps of obtaining the to-be-detected image acquired by the image acquisition module and inputting the to-be-detected image into a tissue nodule detection model may be performed by using another device or devices of another type.

Based on the tissue nodule detection system of this embodiment, target domain data and a to-be-detected image are acquired, the to-be-detected image acquired by the image acquisition module is obtained and inputted into a tissue nodule detection, to obtain nodule location information, where the tissue nodule detection model is obtained according to a tissue nodule detection model training apparatus, and the to-be-detected image and the target image have the same data structure. The tissue nodule detection model training apparatus includes: a training data obtaining module, configured to obtain source domain data and the target domain data acquired by the image acquisition module, the source domain data including a source domain image and an image annotation, and the target domain data including a target image; a feature extraction and training module, configured to perform feature extraction on the source domain image and the target image through a neural network model to obtain a source domain sampling feature and a target sampling feature, and determine a training result according to the source domain sampling feature; a distance parameter determining module, configured to determine a distance parameter between the source domain data and the target domain data according to the source domain sampling feature and the target sampling feature; a source domain loss determining module, configured to determine, according to the training result and the image annotation, a loss function value corresponding to the source domain image; and a model determining module, configured to determine a tissue nodule detection model based on the loss function value, the distance parameter, and the neural network model. A factor of the distance parameter between the source domain data and the target domain data is introduced during determining of a tissue nodule detection model. In this way, the difference between the sampling features of the source domain data and the target domain data that are extracted by using the tissue nodule detection model can be reduced. The detection accuracy can be improved by performing tissue nodule detection on data in the target domain by using the tissue nodule detection model. Therefore, the detection accuracy can be improved by performing tissue nodule detection by using the tissue nodule detection system.

In an embodiment, the system includes an image acquisition device and a tissue nodule detection device, a memory of the image acquisition device stores the image acquisition module, and a memory of the tissue nodule detection device stores the to-be-detected image obtaining module and the detection model detection module.

The image acquisition device is a device acquiring tissue images, for example, may be a CT imaging device. The tissue nodule detection device may include a memory and a processor, the memory storing the to-be-detected image obtaining module and the detection model detection module, and the processor, when calling the modules stored in the memory, may perform the tissue nodule detection method.

Based on the tissue nodule detection system of this embodiment, the step of acquiring target domain data and a to-be-detected image may be performed by using the image acquiring device, and the steps of obtaining the to-be-detected image acquired by the image acquisition module and inputting the to-be-detected image into a tissue nodule detection model may be performed by using the tissue nodule detection device. In this way, the pertinence of the system can be improved by configuring different tissues with different image acquiring devices. Therefore, the accuracy of the system can be further improved.

A person of ordinary skill in the art may understand that all or some of the processes of the methods in the embodiments may be implemented by a computer program instructing relevant hardware (for example, a processor). The computer program may be stored in a non-volatile computer-readable storage medium. When the computer program is executed, the processes of the foregoing method embodiments may be performed. Any reference to a memory, a storage, a database, or another medium used in the various embodiments provided in this application may include a non-transitory and/or volatile memory. The non-transitory memory may include a read-only memory (ROM), a programmable ROM (PROM), an electrically programmable ROM (EPROM), an electrically erasable programmable ROM (EEPROM) or a flash memory. The volatile memory may include a random access memory (RAM) or an external cache. As an illustration instead of a limitation, the RAM is available in various forms, such as a static RAM (SRAM), a dynamic RAM (DRAM), a synchronous DRAM (SDRAM), a double data rate SDRAM (DDRSDRAM), an enhanced SDRAM (ESDRAM), synchronous link (Synchlink) DRAM (SLDRAM), a rambus direct RAM (RDRAM), a direct rambus dynamic RAM (DRDRAM), and a rambus dynamic RAM (DRAM).

The technical features in the foregoing embodiments may be randomly combined. For concise description, not all possible combinations of the technical features in the embodiment are described. However, provided that combinations of the technical features do not conflict with each other, the combinations of the technical features are considered as falling within the scope recorded in this specification.

The foregoing embodiments only describe several implementations of this application, which are described specifically and in detail, but cannot be construed as a limitation to the patent scope of the present disclosure. A person of ordinary skill in the art may make various changes and improvements without departing from the ideas of this application, which shall all fall within the protection scope of this application. Therefore, the protection scope of this application shall be subject to the protection scope of the appended claims.

What is claimed is:

1. A method for training a tissue nodule detection model, performed by a computer device, the method comprising:
obtaining source domain data and target domain data, the source domain data comprising a source domain image and an image annotation, the target domain data comprising a target image with no annotation, and the image annotation being used for indicating location information of a tissue nodule in the source domain image, wherein the source domain data is collected by a first type of device that is different from a second type of device that collects the target domain data, and wherein an image to be detected by the tissue nodule detection model is collected by the second type of device, wherein the first type of device and the second type of device are based on a same radiology technology and are different in at least one of following aspects: a brand name; a model; a sampling distance; a noise level; or a nodule diameter distribution;
performing feature extraction on the source domain image using a neural network model to obtain a source domain sampling feature, performing feature extraction on the target image using the neural network model to obtain a target sampling feature, and determining a model result according to the source domain sampling feature using the neural network model;
determining a distance parameter between the source domain data and the target domain data according to the source domain sampling feature and the target sampling feature, the distance parameter being a parameter describing a magnitude of a data difference between the source domain data and the target domain data;
determining, according to the model result and the image annotation, a loss function value corresponding to the source domain image; and
training the neural network model to obtain a tissue nodule detection model by iteratively reducing a combination of the loss function value and the distance parameter.

2. The method according to claim 1, wherein the distance parameter comprises a maximum mean discrepancy based (MMD-based) discrepancy loss, and wherein determining the distance parameter between the source domain data and the target domain data according to the source domain sampling feature and the target sampling feature comprises determining the MMD-based discrepancy loss between the source domain data and the target domain data according to the source domain sampling feature and the target sampling feature.

3. The method according to claim 2, wherein determining the MMD-based discrepancy loss between the source domain data and the target domain data according to the source domain sampling feature and the target sampling feature comprises:
determining, based on a Gaussian kernel function, the MMD-based discrepancy loss between the source domain data and the target domain data according to the source domain sampling feature and the target sampling feature.

4. The method according to claim 2, wherein determining the MMD-based discrepancy loss between the source domain data and the target domain data according to the source domain sampling feature and the target sampling feature comprises:
determining a first MMD-based discrepancy loss between the source domain data and the target domain data according to the source domain sampling feature and the target sampling feature;
performing target region extraction on the source domain sampling feature, to obtain a source domain candidate region, and performing target region extraction on the target sampling feature, to obtain a target candidate region;
performing, after performing pooling processing on the source domain sampling feature and the source domain candidate region, mapping to obtain a source domain mapping result, and performing, after performing pooling processing on the target sampling feature and the target candidate region, mapping to obtain a target mapping result;
determining a second MMD-based discrepancy loss between the source domain data and the target domain data according to the source domain mapping result and the target mapping result; and
determining the MMD-based discrepancy loss between the source domain data and the target domain data according to the first MMD-based discrepancy loss and the second MMD-based discrepancy loss.

5. The method according to claim 1, wherein training the neural network model to obtain the tissue nodule detection model comprises:
modifying the loss function value based on the distance parameter to generate a modified loss function value; and
training the neural network model to obtain the tissue nodule detection model based on iteratively reducing the modified loss function value.

6. The method according to claim 5, wherein the distance parameter comprises a square of a maximum mean discrepancy (MMD) between the source domain data and the target domain data, and wherein modifying the loss function value based on the distance parameter to generate the modified loss function value comprises performing linear summation of the square of the MMD and the loss function value to obtain the modified loss function value.

7. The method according to claim 1, wherein performing feature extraction on the source domain image using the neural network model to obtain the source domain sampling feature, and performing feature extraction on the target image using the neural network model to obtain the target sampling feature comprises:
segmenting the source domain image, to obtain a source domain tissue region, and segmenting the target image, to obtain a target tissue region; and
performing feature extraction on the source domain tissue region using the neural network model, to obtain the source domain sampling feature, and performing feature extraction on the target tissue region using the neural network model, to obtain the target sampling feature.

8. The method according to claim 1, wherein the source domain image in the source domain data and the target image in the target domain data meet a predetermined quantity relationship.

9. The method according to claim 8, wherein the source domain image in the source domain data and the target image in the target domain data are equal in quantity.

10. The method according to claim 1, wherein performing feature extraction on the source domain image using the neural network model to obtain the source domain sampling feature, performing feature extraction on the target image using the neural network model to obtain the target sampling feature, and determining the model result according to the source domain sampling feature comprises:

performing feature extraction on the source domain image using a first neural network model, to obtain the source domain sampling feature, and determining the model result according to the source domain sampling feature; and performing feature extraction on the target image using a second neural network model, to obtain the target sampling feature, the second neural network model and the first neural network model sharing a same weight.

11. A tissue nodule detection model training apparatus, comprising a memory for storing computer instructions and a processor in communication with the memory, wherein, when the processor executes the computer instructions, the processor is configured to cause the apparatus to:

obtain source domain data and target domain data, the source domain data comprising a source domain image and an image annotation, the target domain data comprising a target image with no annotation, and the image annotation being used for indicating location information of a tissue nodule in the source domain image, wherein the source domain data is collected by a first type of device that is different from a second type of device that collects the target domain data, and wherein an image to be detected by the tissue nodule detection model is collected by the second type of device, wherein the first type of device and the second type of device are based on a same radiology technology and are different in at least one of following aspects: a brand name; a model; a sampling distance; a noise level; or a nodule diameter distribution;

perform feature extraction on the source domain image using a neural network model to obtain a source domain sampling feature, perform feature extraction on the target image using the neural network model to obtain a target sampling feature, and determine a model result according to the source domain sampling feature using the neural network model;

determine a distance parameter between the source domain data and the target domain data according to the source domain sampling feature and the target sampling feature, the distance parameter being a parameter describing a magnitude of a data difference between the source domain data and the target domain data;

determine, according to the model result and the image annotation, a loss function value corresponding to the source domain image; and train the neural network model to obtain a tissue nodule detection model by iteratively reducing a combination of the loss function value and the distance parameter.

12. The apparatus according to claim 11, wherein the distance parameter comprises a maximum mean discrepancy based (MMD-based) discrepancy loss, and wherein, when the processor is configured to cause the apparatus to determine the distance parameter between the source domain data and the target domain data according to the source domain sampling feature and the target sampling feature, the processor is configured to cause the apparatus to determine the MMD-based discrepancy loss between the source domain data and the target domain data according to the source domain sampling feature and the target sampling feature.

13. The apparatus according to claim 12, wherein, when the processor is configured to cause the apparatus to determine the MMD-based discrepancy loss between the source domain data and the target domain data according to the source domain sampling feature and the target sampling feature, the processor is configured to cause the apparatus to:

determine, based on a Gaussian kernel function, the MMD-based discrepancy loss between the source domain data and the target domain data according to the source domain sampling feature and the target sampling feature.

14. The apparatus according to claim 12, wherein, when the processor is configured to cause the apparatus to determine the MMD-based discrepancy loss between the source domain data and the target domain data according to the source domain sampling feature and the target sampling feature, the processor is configured to cause the apparatus to:

determine a first MMD-based discrepancy loss between the source domain data and the target domain data according to the source domain sampling feature and the target sampling feature;

perform target region extraction on the source domain sampling feature, to obtain a source domain candidate region, and perform target region extraction on the target sampling feature, to obtain a target candidate region;

perform, after performing pooling processing on the source domain sampling feature and the source domain candidate region, mapping to obtain a source domain mapping result, and perform, after performing pooling processing on the target sampling feature and the target candidate region, mapping to obtain a target mapping result;

determine a second MMD-based discrepancy loss between the source domain data and the target domain data according to the source domain mapping result and the target mapping result; and determine the MMD-based discrepancy loss between the source domain data and the target domain data according to the first MMD-based discrepancy loss and the second MMD-based discrepancy loss.

15. The apparatus according to claim 11, wherein, when the processor is configured to cause the apparatus to train the neural network model to obtain the tissue nodule detection model, the processor is configured to cause the apparatus to:

modify the loss function value based on the distance parameter to generate a modified loss function value; and train the neural network model to obtain the tissue nodule detection model based on iteratively reducing the modified loss function value.

16. The apparatus according to claim 15, where the distance parameter comprises a square of a maximum mean discrepancy (MMD) between the source domain data and the target domain data, and wherein, when the processor is configured to cause the apparatus to train the neural network model to modify the loss function value based on the distance parameter to generate the modified loss function value, the processor is configured to cause the apparatus to:

perform linear summation of the square of the MMD and the loss function value to obtain the modified loss function value.

17. The apparatus according to claim 11, wherein, when the processor is configured to cause the apparatus to perform feature extraction on the source domain image using the neural network model to obtain the source domain sampling feature, and perform feature extraction on the target image using the neural network model to obtain the target sampling feature, the processor is configured to cause the apparatus to:

segment the source domain image, to obtain a source domain tissue region, and segment the target image, to obtain a target tissue region; and perform feature extraction on the source domain tissue region using the neural network model, to obtain the source domain sampling feature, and perform feature extraction on the target tissue region using the neural network model, to obtain the target sampling feature.

18. The apparatus according to claim 11, wherein the source domain image in the source domain data and the target image in the target domain data meet a predetermined quantity relationship.

19. The apparatus according to claim 18, wherein the source domain image in the source domain data and the target image in the target domain data are equal in quantity.

20. A method for tissue nodule detection, performed by a computer device, the method comprising:

obtaining a to-be-detected image; and inputting the to-be-detected image into a tissue nodule detection model to obtain nodule location information, the tissue nodule detection model being obtained according to a tissue nodule detection model training apparatus, wherein the tissue nodule detection model is trained by:

obtain source domain data and target domain data, the source domain data comprising a source domain image and an image annotation, the target domain data comprising a target image with no annotation, and the image annotation being used for indicating location information of a tissue nodule in the source domain image, wherein the source domain data is collected by a first type of device that is different from a second type of device that collects the target domain data, and wherein an image to be detected by the tissue nodule detection model is collected by the second type of device, wherein the first type of device and the second type of device are based on a same radiology technology and are different in at least one of following aspects: a brand name; a model; a sampling distance; a noise level; or a nodule diameter distribution;

performing feature extraction on the source domain image using a neural network model to obtain a source domain sampling feature, performing feature extraction on the target image using the neural network model to obtain a target sampling feature, and determining a model result according to the source domain sampling feature using the neural network model;

determining a distance parameter between the source domain data and the target domain data according to the source domain sampling feature and the target sampling feature, the distance parameter being a parameter describing a magnitude of a data difference between the source domain data and the target domain data;

determining, according to the model result and the image annotation, a loss function value corresponding to the source domain image; and training the neural network model to obtain a tissue nodule detection model by iteratively reducing a combination of the loss function value and the distance parameter.

* * * * *